(12) United States Patent
Schmid et al.

(10) Patent No.: US 7,267,547 B2
(45) Date of Patent: Sep. 11, 2007

(54) DEVICE FOR REGULATED HEATING OF MEDIA IN A DENTAL HANDPIECE

(75) Inventors: Gerhard Schmid, Mittelbiberach (DE); Gerd Löhn, Biberach-Risseg (DE); Franz Liebhardt, Ochsenhausen (DE); Hubert Mösslang, Oberdischingen (DE)

(73) Assignee: Kaltenbach & Voigt GmbH & Co. KG, Biberach (DE)

( * ) Notice: Subject to any disclaimer, the term of this patent is extended or adjusted under 35 U.S.C. 154(b) by 627 days.

(21) Appl. No.: 10/636,031

(22) Filed: Aug. 7, 2003

(65) Prior Publication Data
US 2004/0076923 A1   Apr. 22, 2004

(30) Foreign Application Priority Data
Aug. 16, 2002   (DE) ................ 102 37 520
Dec. 19, 2002   (DE) ................ 102 59 798

(51) Int. Cl.
A61C 3/00   (2006.01)
(52) U.S. Cl. .......................... 433/32; 433/80
(58) Field of Classification Search .......... 433/80, 433/32, 27, 82
See application file for complete search history.

(56) References Cited

U.S. PATENT DOCUMENTS 4,531,912 A * 7/1985 Schuss et al. ............... 433/80
4,886,452 A * 12/1989 Lohn ........................ 433/32
5,123,839 A   6/1992 West ......................... 433/32
5,271,087 A   12/1993 Schmid ...................... 392/485

FOREIGN PATENT DOCUMENTS

| DE | 39 01 198 A1 | 9/1990 |
| DE | 195 48 444 C1 | 3/1997 |
| EP | 525 443 B1 | 2/1993 |

* cited by examiner

Primary Examiner—Melba Bumgarner
(74) Attorney, Agent, or Firm—Marshall, Gerstein & Borun LLP

(57) ABSTRACT

A device for regulated heating of media in a dental handpiece has at least one media line which can be opened via a switch, a heating element associated with the media line, a temperature sensor detecting the temperature of the medium and a regulation circuit which is connected with the temperature sensor and controls the heating element in dependence upon the sensor signals. After actuation of the switch the heating element is operated for a short period of time at a predetermined heating power independent of the output signal of the regulation circuit, in order to heat the medium as rapidly as possible to the required temperature.

26 Claims, 6 Drawing Sheets

DEVICE FOR REGULATED HEATING OF MEDIA IN A DENTAL HANDPIECE

Figure 1:
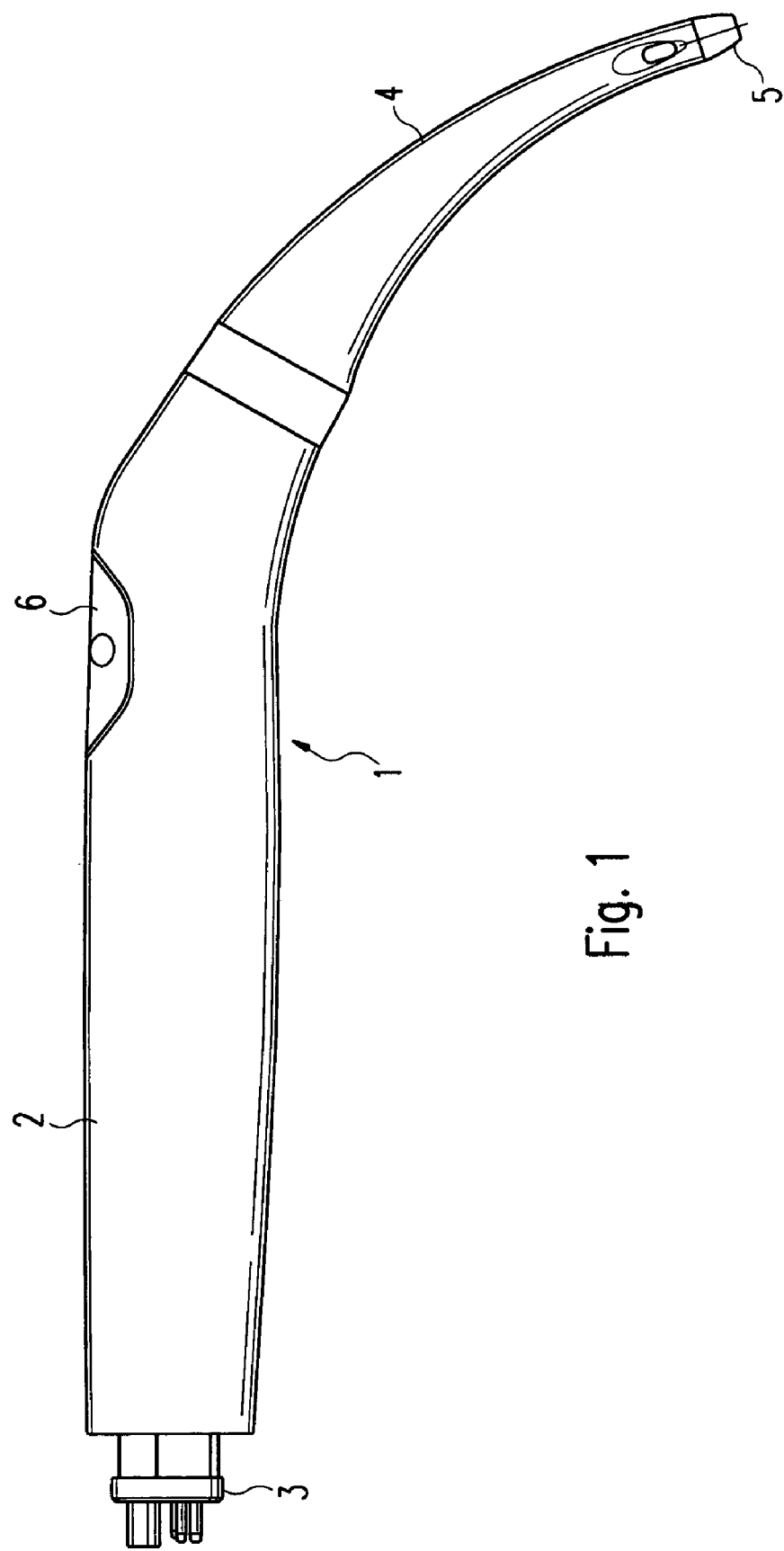

The present invention relates to a device for regulated heating of media in a dental handpiece, in particular in a dental spray handpiece.

Spray handpieces are put to use at dental treatment stations for various purposes, for example for blowing clear treatment sites in the mouth of the patient or for rinsing. Thereby, as a rule, spray handpieces offer the possibility of delivering a water-air mixture in the form of a spray for the cooling or cleaning of treatment sites. For this purpose, the handpiece has a nozzle via which water, air, or water and air simultaneously are issued. Both media should thereby be heated to approximately body temperature in order to cause in the patient, in whose mouth they are put to use, no reflex or defense reactions. Normally, the heating of the individual media can also be switched off in order to deliberately deliver cold media and therewith, for example after certain treatments, to test reflexes of the patient.

In order to heat the media issued by the spray handpiece to a temperature which remains as uniform as possible, it is known from EP 0 525 443 A1 to adapt the heating power to the media consumption. For this purpose, the power delivered to the heating elements is varied with the aid of a pulse packet controller, which includes a switching element lying in the heating current circuit and actuable by a setting member, between a lower limit, which corresponds to heating being switched off, and a maximum heating power. The possibility of altering the heating power exists also with a handpiece known from DE 195 48 444 C1. Here, in dependence upon the throughflow quantity of the issued medium there is derived an electrically processable parameter with the aid of a characteristic line stored in a controller component, which parameter corresponds to a heating power necessary for the attainment of the desired media temperature.

Since, with the handpiece known from DE 195 48 444 C1, the heating power required to obtain a desired temperature is determined with the aid of a predetermined characteristic line, external influences, such as for example a temperature variation of the medium made available from an initial reservoir, can no longer be taken into account. Thus, although complicated measures for exact temperature regulation are avoided, there is however accepted through this a certain inexactitude in the temperature of the issued medium which is in the end attained.

In order to set the temperature of the medium as exactly as possible, with a handpiece known from DE 39 01 198 A1 there are provided temperature sensors which are arranged within the handpiece and very close to the exit nozzle. These temperature sensors are connected with regulating units which are likewise accommodated in the handpiece, whereby the regulating units control the heating elements in dependence upon the sensor signals. With the aid of this regulation circuitry the temperature of the issued media can thus be set very exactly. Since, moreover, the temperature sensors are arranged close to the outlet nozzle of the handpiece, a cooling of the media on the way from the heating element to the nozzle can likewise be taken into account.

The employment of a regulation circuit for the media heating thus makes possible a very precise setting of the media temperature; since the regulation however involves a certain delay effect the period of time over which, after switching on of air and/or water, the desired final temperature for the two media is attained is lengthened. Beyond this, with a simultaneous temperature regulation of both media, energy consumption is increased.

The object of the present invention is so to improve the known arrangements for the heating of the media in a dental handpiece that after a switching on of the media these are heated as rapidly as possible to the desired intended temperature.

This object is achieved by means of a device according to the invention. The device has a first at least one media line which can be opened by a switch, a heating element associated with the media line, a temperature sensor which detects the temperature of the medium, and a regulation circuit. The regulation circuit is thereby connected with the temperature sensor and controls the heating element in dependence upon the sensor signals, as is already known from DE 39 01 198 A1.

The solution in accordance with the invention consists in that after an actuation of the switch, the heating element is operated for a short period of time at a predetermined heating power, independently of the output signal of the regulation circuit. Through this, the heating is in any event switched on for a short period of time independently of the output signal of the regulation circuit, whereby through the suppression of the regulation in the initial stage the medium emerging from the output nozzle is heated to the desired intended temperature in as short as possible time.

A further object of the present invention consists in keeping the energy consumption of the media heating as low as possible.

In accordance with a second aspect of the present invention, this object is achieved in that with a device for regulated heating of air and water in a dental handpiece, in the case of a simultaneous actuation of the switches for air and for water, the heating element for the air media line is switched off. In the case of a spray operation of the handpiece, only the water is thus heated, whilst the additional heating of the air is omitted, in order not to use energy unnecessarily. The switching off of the air heating thereby has only an insignificant effect on the temperature of the spray, since this is in any event virtually completely determined by the water temperature.

The period of time of the above-described suppression of the heating regulation is preferably dependent upon the switch-on interval of the switch for the media line. In the case that the regulation circuit for the operation of the heating element switches, with the aid of transistor, an optotriac, which in turn switches a power triac for the heating current of the heating element, this can be achieved in that an RC member is connected to the base terminal of the transistor, which RC member after an actuation of the switch suppresses the output signal of the regulation circuit for a short period of time. The discharge resistor for the capacitor of the RC member now ensures that the suppression time of the regulation is made dependent upon the switch-on interval of the switch. The period of time for which the regulation is suppressed is thereby preferably ca. one second, whereby this suppression of the regulation is preferably provided exclusively for the heating of the air.

The temperature sensors and the other electronic components of the heating device in accordance with the invention are preferably arranged completely within the dental handpiece, in order to be able to fully exploit the advantages offered through the temperature regulation.

A further aspect of the present invention relates to the power loss arising in the electronic components of the heating device, in particular at the power triac for controlling the heating elements. In order to minimize this power loss, the loss heat arising at the power triac for the water heating can be directly returned to the water to be heated. The return is effected with the aid of a heat exchanger element which is connected to the water line and thermally coupled with the power triac. Through this, on the one hand the energy usage of the media heating is optimized, on the other hand the heat discharge from the power triac is improved, and therewith an undesired heating of the handpiece avoided.

Figure 2:
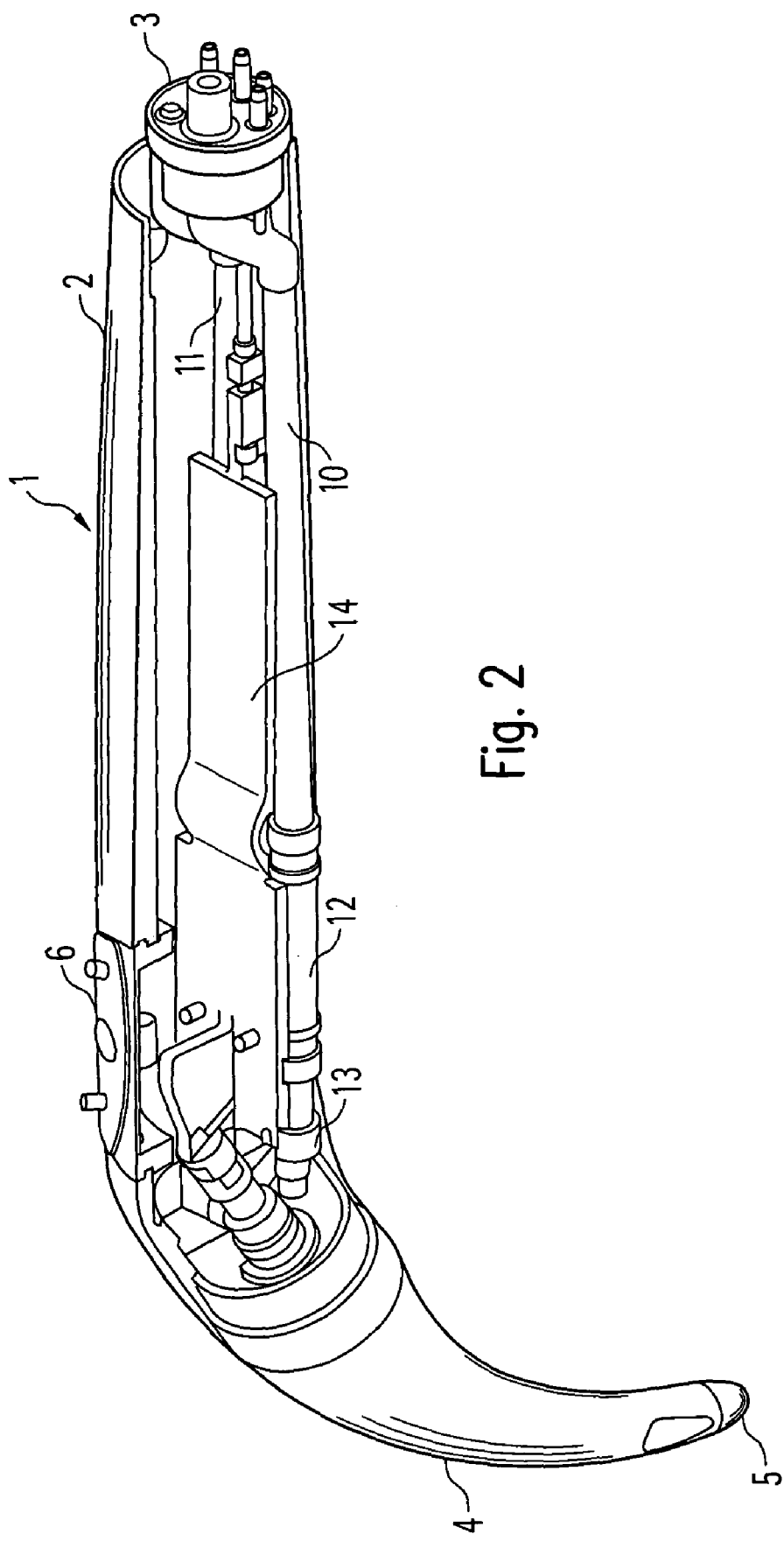
Figure 3:
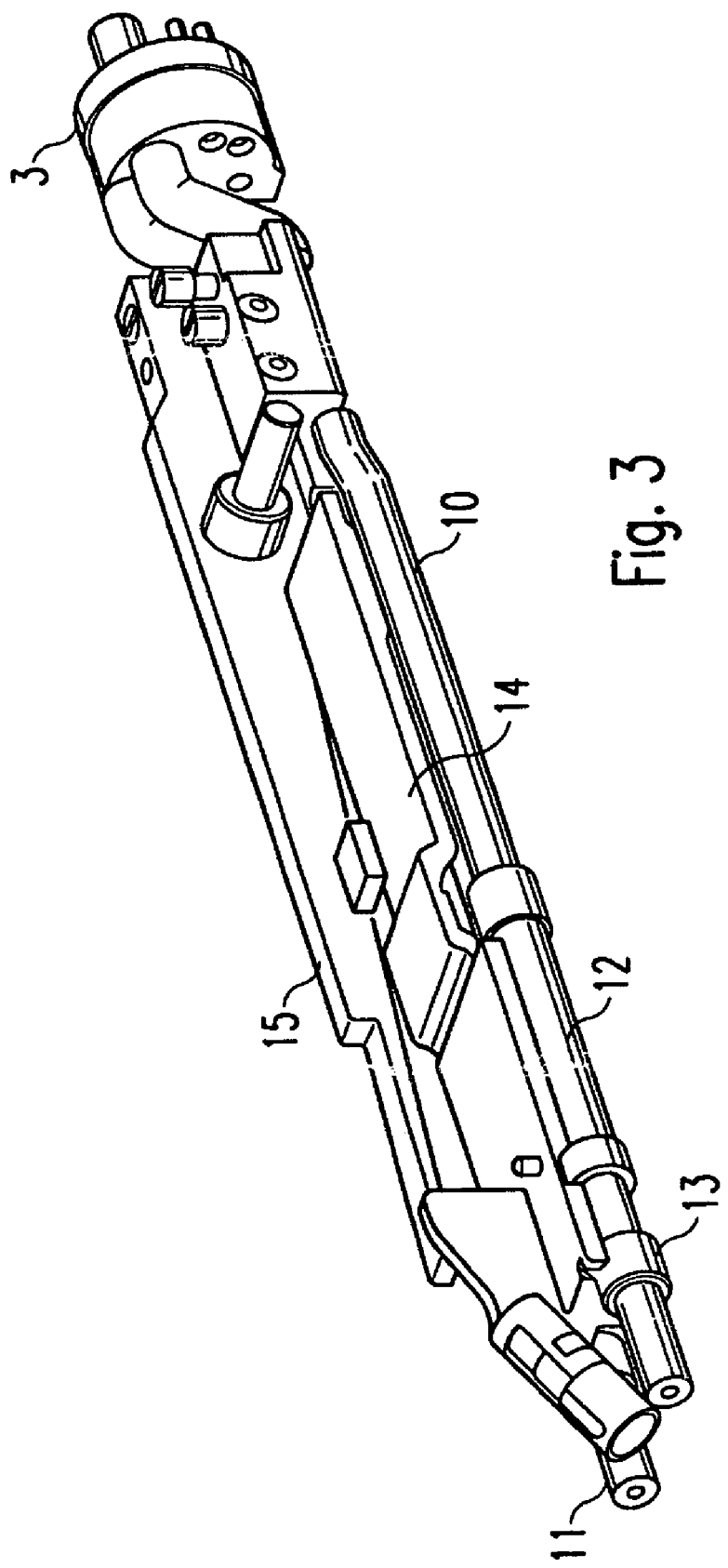
Figure 4A:
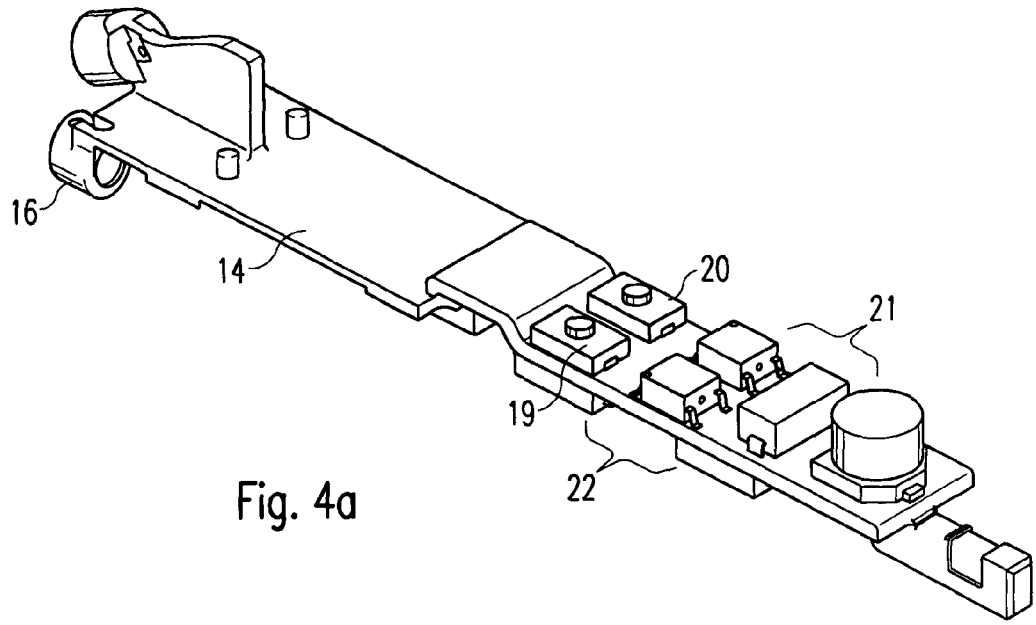
Figure 4B:
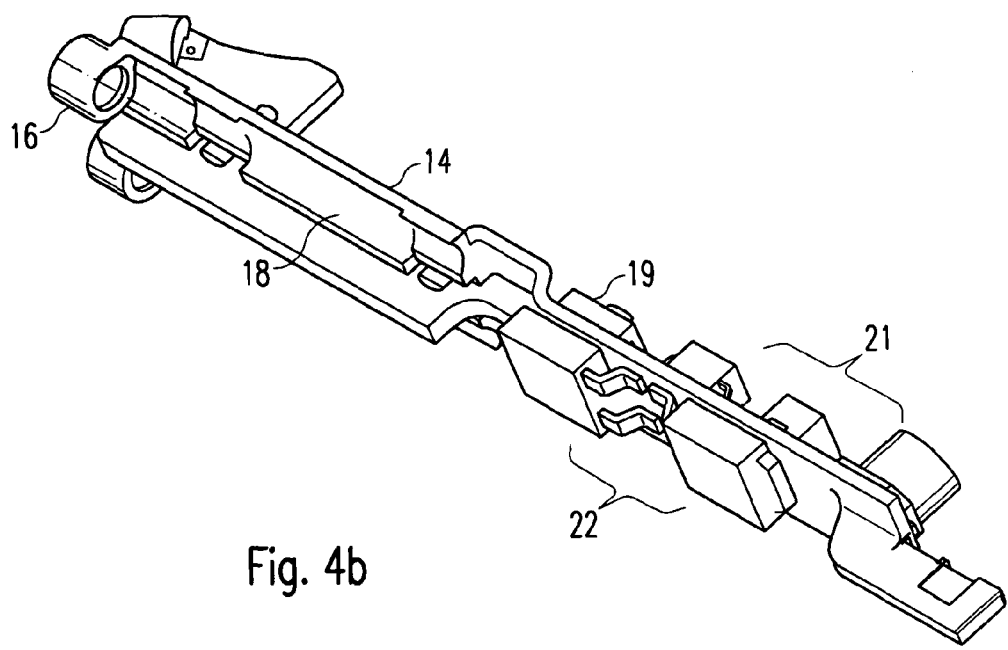
Figure 5:
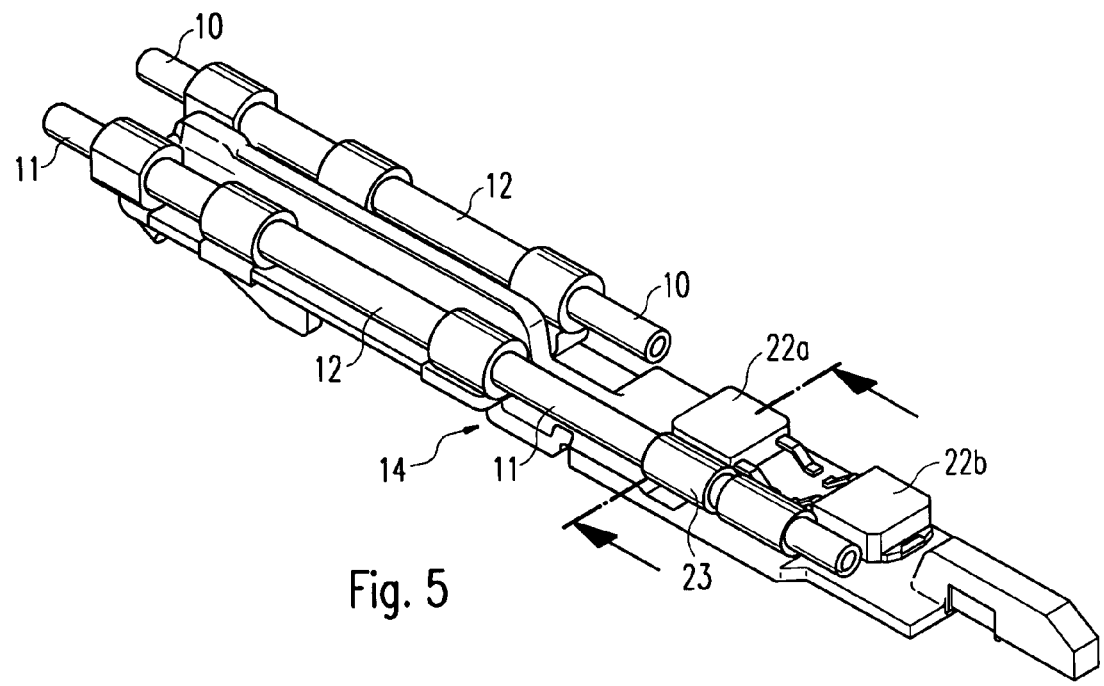
Figure 6A:
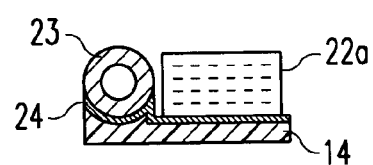
Figure 6B:
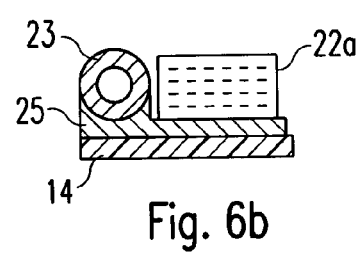
Figure 6C:
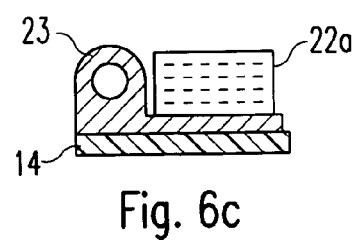
Figure 7:
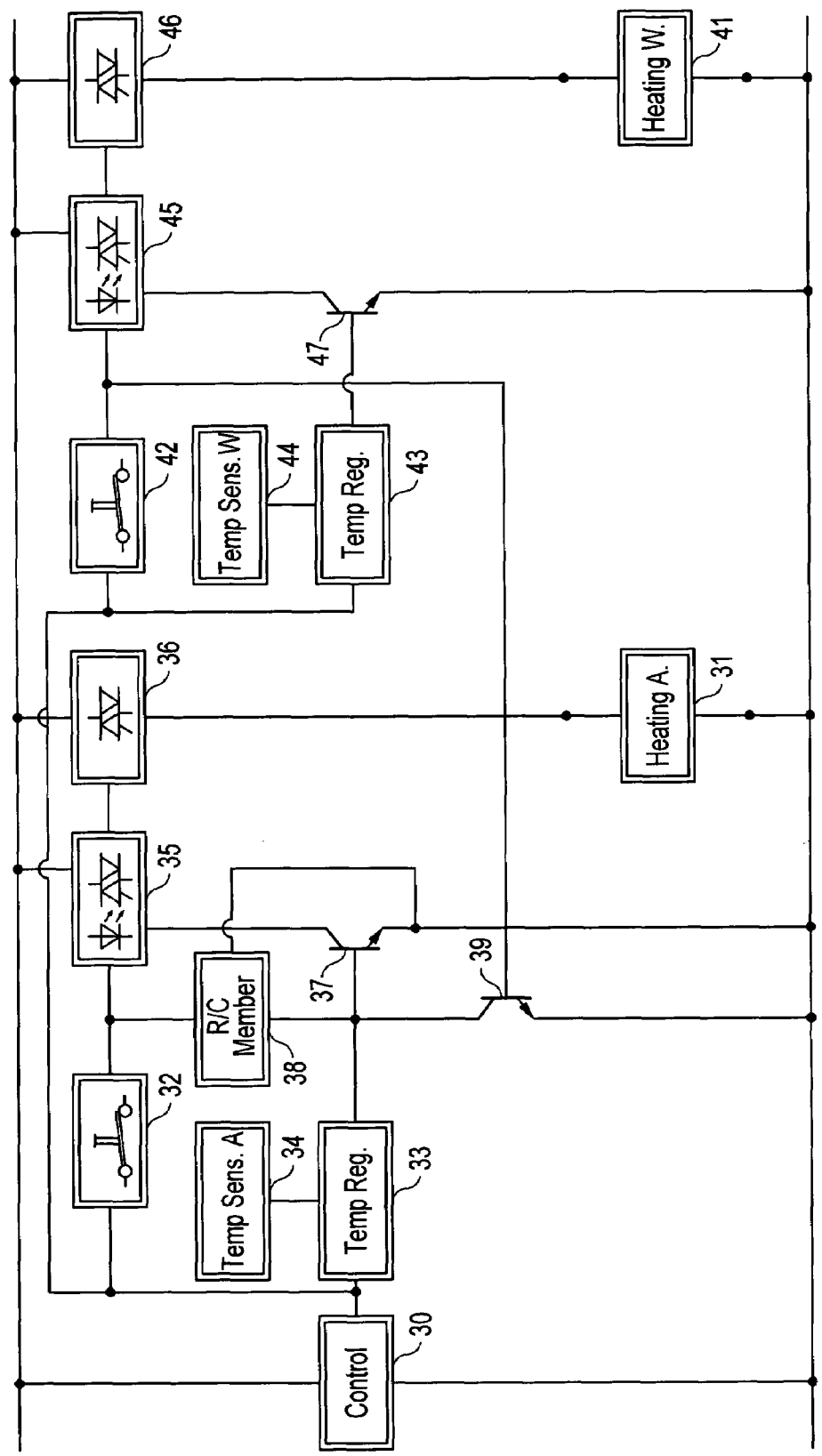

Below, the invention will be described in more detail with reference to the accompanying drawings. There is shown:

FIG. 1 a dental spray handpiece, with which the device in accordance with the invention is to be put to use, in a side view;

FIG. 2 the dental spray handpiece in a part section;

FIG. 3 the main elements of the heating device in accordance with the invention, in a perspective view;

FIGS. 4a, 4b different views of a circuit board which carries the main elements of the heating device;

FIG. 5 the underside of the circuit board for a preferred exemplary embodiment;

FIGS. 6a-c various variants of the exemplary embodiment illustrated in FIG. 5, in section;

FIG. 7 a block circuit diagram of the heating device in accordance with the invention.

The dental spray handpiece 1 illustrated in FIG. 1 is comprised of an elongate grip body 2, to the rear side of which there is arranged a media coupling 3, via which the handpiece 1 can be connected to a conventional supply hose. The media coupling 3 has for this purpose individual connection pieces for the media air and water as well as further supply lines, for example for current and light.

At the forward end of the grip body 2 there is arranged a bowed nozzle body 4 at the free end of which the nozzle 5 for the issue of air and/or water is located. Via the nozzle body 4, beyond this, light can also be directed onto the site to be treated.

In the forward region of the elongate grip body 2 there are located on its upper side a touch panel 6 with two actuating elements for the media air and water. Via the actuating elements, the valve for the corresponding media line can be opened and a switch for the corresponding media heating can be closed. With a simultaneous actuation of both actuating elements, the media lines for air and water are simultaneously open, so that air and water can be issued in the form of a spray with the aid of the nozzle 5 arranged at the forward end of the nozzle body 4.

FIG. 2 shows a part of the elements arranged of the interior of the handpiece 1. For reasons of clarity the trip levers actuable via the touch panel 6 for opening the media lines and switching on the media heatings are not illustrated, just as the electronic components of the temperature regulation are not. The two media lines 10 and 11 for air and water run within the grip body 2 in longitudinal direction. Both media lines 10 and 11 are connected at their rearward end with the media coupling 3. In the forward region of the media line 10 for air there is located a heating element 12 with the aid of which the air flowing through the media line 10 is warmed. The heating element may be for example a conventional heating cartridge which continues the media line 10 so that the air is heated upon flowing through the heating cartridge 12. In a similar manner there is also provided a corresponding heating element for the media line 11 for water.

In order to make possible a temperature regulation there is arranged at the forward end of the media line 10 for air a temperature sensor 13 which measures of the temperature of the air after flowing through the heating element 12. This arrangement of the temperature sensor 13 is of advantage since on the one hand measurement takes place very close to the heating element 12 and thus an unintended burnout of the heating element 12 is avoided. On the other hand, the sensor 13 is located very close to the outlet point of the medium so that a cooling of the medium along the final stretch of path up to the nozzle 5, which cannot be avoided, remains negligibly small. A second temperature sensor for the media line 11 for water is arranged in similar manner at the opposite side of the grip body.

The electronic components of the media heating in accordance with the invention are arranged on an elongate base circuit board 14 which is to explained in more detail below. In this connection, FIG. 3 shows again the main components of the device in accordance with the invention for the heating of the media. Thereby, one of the two trip levers 15 is also illustrated, which upon an actuation of the corresponding actuation element on the outside of the handpiece is pressed down, on the one hand to open the valve for the corresponding media line and on the other hand to activate the heating for this medium. The activation of the heating is effected by means of a projection, projecting from the lever towards the interior which presses down upon a contact (not shown) located on the base circuit board 14.

The base circuit board 14 is an injection molded circuitry carrier, a so-called 3D-MID (molded interconnected device). Such circuitry carriers combine both mechanical and also electronic functions in a single element and correspondingly offer the possibility of keeping the dimensions of the overall device as small as possible. Through this, the installation of the complete heating device in the handpiece is made possible. From the different views of the base circuit board 14 in FIGS. 4a and 4b it can be understood that at its underside there are provided guides 18 for the tube-shaped heating elements, so that a reliable attachment is made possible. At the forward end there are further located tube-like connection pieces 16 to which the outputs of the heating elements are connected. Within these connecting pieces 16 there are also located the temperature sensors with the aid of which the temperature of the media issued by the heating elements is determined.

In the rearward region of the base circuit board 14 there are arranged in the one hand the two contacts 19 and 20 which upon pressing down of the corresponding trip lever activate the associated media heatings. Further, there are arranged on the upper and lower sides the further electronic components of the heating, generally designated by the reference signs 21 and 22, in particular the two power triacs 22 explained below, for operating the media heatings 12. The electrical connection between the various components and contacts is established via conductor lines which run on the upper and lower sides of the base circuit board 14 and through the circuit board 14.

FIG. 5 shows a particularly preferred variant of the heating device in accordance with the invention. In order to minimize the not be neglected power loss of the heating, the loss heat arising at the power triac 22a for the water heating is directly returned to the water to be heated. The return is effected with the aid of a heat exchanger element 23 that is connected to the water line 11. Through this on the one hand the energy usage of the media heating is optimized, on the other hand the heat removal from the power triac 22a is improved and therewith an undesired heating of the handpiece prevented. This heat return is preferably provided solely for the water heating.

For the return of the loss heat, various variants are conceivable which are to be explained below with reference to the sectioned illustrations in FIGS. 6a to 6c.

With the first variant according to FIG. 6a, the base circuit board 14 is so shaped that the heat exchanger element 23 is fixed in its position and a heat exchange surface is formed between heat exchanger element 23 and power triac 22a. The bearing surfaces of the heat exchanger element 23 and power triac 22a, and the region of the base circuit board 14 lying therebetween, are provided with a metallized layer 24. This layer 24, which is formed analogously to conductor tracks, ensures a thermal connection and thus a heat discharge from the power triac 22a to the heat exchanger element 23. This first variant distinguishes itself in particular through a simple construction.

With the second variant according to FIG. 6b there is provided an additional cooling body 25 as heat transport means, which is so shaped that a heat exchange surface between power triac 22a and heat exchanger element 23 which is as great as possible is formed. The cooling body 25 is placed between the base circuit board 14 on the one hand and the power triac 22a and the heat exchanger element 23 on the other hand and makes possible, in comparison to the variant illustrated in FIG. 6a, improved heat conduction.

Finally, with the third variant according to FIG. 6c, the heat exchanger element 23 is formed in one piece and so configured that the power triac 22a can be arranged directly on this. This third variant makes possible a further improved transfer of heat. The heat coupling of all three variants can, finally, be further improved in that in the region of the bearing surfaces of the power triac 22a and of the heat exchanger element 23 there is additionally applied a heat conducting paste.

On the basis of the block circuit diagram in FIG. 7 the manner of functioning of the heating device in accordance with the invention is to be explained below. Thereby, for the control and heating solely a single supply voltage of preferably 24 Volts AC is needed, to which all components of the heating device, that is both the regulation units and also the heating elements, are connected.

The block diagram in FIG. 7 shows a control component 30 which is responsible overall for the activation of the heating device, and the two heating and regulation circuits for air and for water. Both heating circuits thereby consist firstly of a switch 32 or 42, which upon actuation of the corresponding actuating element on the upper side of the handpiece and the opening of the media valve, are closed via a trip lever and therewith the corresponding media heating is switched on. The heating elements 31 and 41 for air and for water are each operated via a power triac 36 or 46 via which the power for the two heating elements 31, 41 is set. The control of the power triac 36 or 46 is effected in each case by means of an optotriac 35 or 45 switching at zero crossings, with the aid of which a fault suppression is made possible. The control of the optotriac 35 or 45 is effected by means of control circuits 33 or 43 which control, in dependence upon the required heating power, a transistor 37 or 47, to the output of which the optotriac 35 or 45 is connected.

The regulation circuits 33 and 43 are in each case connected with a corresponding temperature sensor 34 or 44 and generate in dependence upon the sensor signals control signals for the respective transistors 37 and 47. With the aid of these control signals the two power triacs 36 and 46 are thus operated with the power required for the attainment of a desired temperature for the medium.

The media heating for air has, in comparison with the media heating for water, additionally also an RC member 38 which is connected with the base terminal of the transistor 37 and connects this with the output of the switch 32. Upon a closing of the switch 32—that is, upon a switching on of the media heating for the air—the RC member 38 has the effect that the output signals of the regulation circuit 33 are suppressed for a short period of time and the transistor 37 is so controlled that the heating element 31 is operated at maximum heating power for a short period of time. Through this it is achieved that upon an opening of the media line the air is heated rapidly to the desired temperature. Since the capacitor of the RC member discharges again, with a certain delay, after the opening of the switch 32, this suppression time for the regulation of the heating can be made dependent upon the switch-on interval of the switch. Preferably the period of time for the suppression of the temperature regulation of the air heating is about a second.

A further special feature of the heating consists in that upon closure of the switch 42 for the water media heating, an additional transistor 39 is so controlled that the air media heating is completely switched off. This has the consequence, in the case that the switches for air and water are simultaneously closed in order to operate the spray handpiece in spray operation, that exclusively the heating for the water is activated and correspondingly the energy for an additional heating of the air is saved. Since the temperature of the spray is, due to the high thermal coefficient of the water, in any event determined primarily through the water temperature, the omission of the air heating has no substantial temperature change as a consequence, but reduces the energy consumption of the media heating.

The present invention thus makes possible an effective and energy saving possibility for setting the temperature of the media issued from a spray handpiece to a desired value. Thereby, the device can be completely and space-savingly integrated into a handpiece.

The invention claimed is:

1. Device for regulated heating of a medium in a dental handpiece, comprising
    a) a first media line which can be opened via a first switch,
    b) a heating element associated with the first media line,
    c) a temperature sensor detecting the temperature of the medium, and
    d) a regulation circuit connected with the temperature sensor and which controls the heating element in dependence upon signals provided by the temperature sensor, the regulation circuit including a capacitor,
    wherein the heating element is, after actuation of the switch, operable for a short period of time at a predetermined heating power independent of an output signal of the regulation circuit, and
    wherein the duration of the short period of time during which the heating element is operated at a predetermined heating power is dependent upon a delay of the capacitor.

2. Device according to claim 1,
    wherein
    the device comprises a second media line which can be opened by a second switch, with which second media line there are associated a second heating element, a second temperature sensor, and a second regulation circuit, the second regulation circuit controlling the second heating element in dependence upon sensor signals of the second temperature sensor.

3. Device according to claim 2,
    wherein
    the first media line is provided for the delivery of air and the second media line is provided for the delivery of water, wherein upon simultaneous actuation of the first and second switches the heating element for the first media line is switched off.

4. Device according to claim 1, wherein the temperature sensor is arranged directly in the first media line.

5. Dental spray handpiece for the delivery of air and/or water, comprising
a heating device for regulated heating of the air and or water in accordance with claim 1.

6. Dental spray handpiece according to claim 5,
the heating device including a set of electronic components,
wherein
the temperature sensor or sensors and the set of electronic components of the heating device are arranged completely within the handpiece.

7. Device for regulated heating of a medium in a dental handpiece, comprising
a first media line for air which can be opened via a first switch and a second media line for water which can be opened via a second switch,
there being associated with each media line a respective heating element, a respective temperature sensor detecting the temperature of the respective medium, and a respective regulation circuit connected with a corresponding temperature sensor,
the regulation circuits controlling the respective heating elements in dependence upon signals provided by the respective temperature sensor,
wherein
the regulation circuit is configured such that upon simultaneous actuation of the first switch and the second switch, the regulation circuit switches off the heating element for the first media line for air,
wherein, after actuation of the first switch the heating element associated with the first media line is operable for a short period of time at a predetermined heating power independent of an output signal of the regulation circuit associated with the first media line,
the regulation circuit including a capacitor, wherein a suppression time of the output signal is dependent upon a delay of the capacitor.

8. Device according to claim 7,
wherein
the temperature sensors are arranged directly in their respective associated media lines.

9. Device for regulated heating of a medium in a dental handpiece, comprising
a first media line for air which can be opened via a first switch and a second media line for water which can be opened via a second switch.
there being associated with each media line a respective heating element, a respective temperature sensor detecting the temperature of the respective medium, and a respective regulation circuit connected with a corresponding temperature sensor,
the regulation circuits controlling the respective heating elements in dependence upon signals provided by the respective temperature sensor,
wherein
the regulation circuit is configured such that upon simultaneous actuation of the first switch and the second switch, the regulation circuit switches off the heating element for the first media line for air, and
wherein
the regulation circuit or circuits control is via a transistor, an optotriac switching at zero crossing, which optotriac switches a power triac for a heating current of the heating element concerned.

10. Device according to claim 9,
wherein
there is connected to a base terminal of the transistor for air heating an RC member which after actuation of the first switch for the heating element associated with the first media line suppresses an output signal of the regulation circuit for a short period of time.

11. Device according to claim 9,
wherein
there is provided in the media line for water a heat exchanger element which is thermally coupled with the power triac for returning heat loss arising at the power triac.

12. Device according to claim 11,
wherein
the power triac and the heat exchanger element are arranged on a common circuit board and connected with one another via a metallized layer.

13. Device according to claim 11,
wherein
the power triac and the heat exchanger element are arranged on a common cooling body.

14. Device according to claim 11,
wherein
the heat exchanger element forms a bearing surface for the power triac.

15. Device according to claim 11,
wherein a heat conductive paste is applied
in a region of the bearing surfaces for the power triac and for the heat exchanger element.

16. Device for the regulated heating of a medium in a dental handpiece, comprising
a) at least one media line which can be opened via a switch,
b) a heating element associated with the media line,
c) a temperature sensor detecting the temperature of the medium,
d) a regulation circuit connected with the temperature sensor and which controls the heating element in dependence upon signals provided by the temperature sensor, the regulation circuit including a first set of electronic components,
and,
e) a heat exchanger element provided in the media line which for the return of heat loss arising at the first set of electronic components of the regulation circuit is thermally coupled with the media line.

17. Dental spray handpiece for the delivery of air and/or water, comprising a heating device for regulated heating of the air and or water in accordance with claim 16.

18. Dental spray handpiece according to claim 17, the heating device including a second set of electronic components, wherein the temperature sensor or sensors and second set of electronic components of the heating device are arranged completely within the handpiece.

19. Device for regulated heating of a medium in a dental handpiece, comprising
a) at least a first media line which can be opened via a first switch,
b) a heating element associated with the first media line,
c) a temperature sensor detecting the temperature of the medium, and d) a regulation circuit connected with the temperature sensor and which controls the heating element in dependence upon signals provided by the temperature sensor, wherein the heating element is configured to operate for a short period of time after actuation of the first switch at a predetermined heating power independent of an output signal of the regulation circuit, and wherein the regulation circuit or circuits control is via a transistor, an optotriac switching at zero crossing, which optotriac switches a power triac for a heating current of the heating element concerned.

20. Device according to claim 19, wherein there is connected to a base terminal of the transistor for air heating an RC member which after actuation of the first switch suppresses the output signal of the regulation circuit for a short period of time.

21. Device according to claim 19, wherein the first media line is provided for delivery of water, wherein there is provided in the first media line a heat exchanger element which is thermally coupled with the power triac for returning heat loss arising at the power triac.

22. Device according to claim 21, wherein the power triac and the heat exchanger element are arranged on a common circuit board and connected with one another via a metallized layer.

23. Device according to claim 21, wherein the power triac and the heat exchanger element are arranged on a common cooling body.

24. Device according to claim 21, wherein the heat exchanger element forms a bearing surface for the power triac.

25. Device according to claim 21, wherein a heat conductive paste is applied in a region of the bearing surfaces for the power triac and for the heat exchanger element.

26. A dental spray handpiece for the delivery of air and/or water, comprising a first media line for air which can be opened via a first switch and a second media line for water which can be opened via a second switch, there being associated with each media line a respective heating element, a respective temperature sensor detecting the temperature of the respective medium, and a respective regulation circuit connected with a corresponding temperature sensor, the regulation circuits controlling the respective heating elements in dependence upon signals provided by the respective temperature sensor, and a heating device including a set of electronic components, wherein the temperature sensor or sensors and the set of electronic components of the heating device are arranged completely within the handpiece, wherein the regulation circuit is configured such that upon simultaneous actuation of the first switch and the second switch, the regulation circuit switches off the heating element for the first media line for air.

* * * * *